(12) United States Patent
Ackman et al.

(10) Patent No.: US 6,586,478 B2
(45) Date of Patent: Jul. 1, 2003

(54) METHODS AND COMPOSITIONS FOR IMPROVING SLEEP

(75) Inventors: C. Bruce Ackman, Kingston (CA); Michael A. Adams, Kingston (CA); Jeremy P. W. Heaton, Gananoque (CA); Jodan D. Ratz, Kingston (CA)

(73) Assignee: Cellegy Canada, Kingston (CA)

( * ) Notice: Subject to any disclaimer, the term of this patent is extended or adjusted under 35 U.S.C. 154(b) by 0 days.

(21) Appl. No.: 09/791,127

(22) Filed: Feb. 22, 2001

(65) Prior Publication Data

US 2002/0015740 A1 Feb. 7, 2002

Related U.S. Application Data

(60) Provisional application No. 60/184,087, filed on Feb. 22, 2000, and provisional application No. 60/236,727, filed on Oct. 2, 2000.

(51) Int. Cl.$^7$ .................. A16P 25/00; A61K 31/04; A61K 31/198; A61K 38/06; A61K 31/519
(52) U.S. Cl. .................. 514/738; 514/464; 514/564; 514/18; 514/664; 514/259; 514/263; 514/401; 514/247; 514/355; 514/502; 514/562; 514/236.8; 514/408; 514/236.2; 514/674; 514/258; 514/424; 514/248; 514/283; 514/261; 514/262; 514/299; 514/303; 514/923
(58) Field of Search .................. 514/509, 923, 514/469, 283, 738, 261, 564, 262, 18, 299, 664, 303, 259, 263, 401, 247, 355, 502, 562, 236.8, 408, 236.2, 674, 258, 424, 248

(56) References Cited

U.S. PATENT DOCUMENTS

| | | | | |
|---|---|---|---|---|
| 5,968,911 A | * | 10/1999 | Lawson et al. | ............... 514/46 |
| 6,155,976 A | * | 12/2000 | Sackner et al. | ............. 600/300 |

FOREIGN PATENT DOCUMENTS

| | | |
|---|---|---|
| EP | 0 846 465 A1 | 6/1998 |
| WO | WO 00/9130 A3 | 2/2000 |
| WO | WO 00/67754 A1 | 11/2000 |

OTHER PUBLICATIONS

Berraueta et al., "Successful treatment of shoulder pain syndrome due to supraspinatus tendinitis with transdermal nitroglycerin." 1996, Pain vol. 66, p. 63–67.*

Drug Facts and Comparisons 1998, p. 1782–1783.*

Drug Facts and Comparisons 1999, p. 890.*

Notification of Transmittal of The International Search Report or the Declaration with Copy of International Search Report.

Levente Kapas and James M. Krueger, Intracerebroventricular (ICV) Injection of the Nitric Oxide Donors Snap and Sin–1 Induces Sleep in Rats, Department of Physiology and Biophysics, University of Tennessee, Memphis, TN 38163 XP–001027364.

Levente Kapas and James M. Krueger, Nitric Oxide Donors SIN–1 and SNAP Promote Nonrapid–Eye–Movement Sleep in Rats, Department of Physiology and Biophysics, University of Tennessee, Memphis, TN 38163, Brain Research Bulletin, vol. 41, No. 5, pp. 293–298, 1996 XP–001055637.

International Search Report of International Application No. PCT/IB 99/01389.

Aoki E. et al., "Localization of nitric oxide–related substances in the peripheral nervous tissues", *Brain Res.* 1993 620:142–145.

Berge S.M. et al., "Pharmaceutical Salts", *J. Pharmaceutical Sciences* 1977 66:1–19.

Buchwald D., "Fibromyalgia and Chronic Fatigue Syndrome. Similarities and Differences", *Rheum. Dis. Clin. North Am.* 1996 22 (2):219–243.

Butler A.R. et al., "NO, nitrosonium ions, nitroxide ions, nitrosothiols and iron–nitrosyls in biology: a chemist's perspective", *Trends Pharmacol. Sci.* 1995 16:18–22.

Harding S.M., "Sleep in Fibromalgia Patients:Subjective and Objective Findings", *Am. J. Med. Sci.* 1998 315 (6):367–376.

Stamler J.S. et al., "Biochemistry of Nitric Oxide and Its Redox–Activated Forms", *Science* 1992 258:1898–1902.

\* cited by examiner

*Primary Examiner*—Edward J. Webman
(74) *Attorney, Agent, or Firm*—Townsend and Townsend and Crew LLP

(57) ABSTRACT

Methods and compositions for improving sleep in individuals with sleep disorders or other conditions which interfere with normal sleep via administration of a NO-mimetic are provided.

15 Claims, No Drawings

METHODS AND COMPOSITIONS FOR IMPROVING SLEEP

INTRODUCTION

This application claims the benefit of priority of U.S. provisional patent application Ser. No. 60/236,727, filed Oct. 2, 2000 and U.S. provisional patent application Ser. No. 60/184,087, filed Feb. 22, 2000.

FIELD OF THE INVENTION

The present invention relates to methods and compositions for improving sleep in individuals suffering from sleep disorders (SDs) and other conditions which interfere with sleep. More particularly, the present invention relates to methods of improving sleep in individuals through administration of low doses of nitric oxide-mimetics (NO-mimetics).

BACKGROUND OF THE INVENTION

Sleep is a complex process with many parts of the nervous system being involved in controlling it and influencing its different stages. Stages or levels of sleep include drowsiness, light sleep, deep sleep, and dream sleep. It is possible to identify which stage of sleep a person is in by measuring different activities of the brain (central nervous system) and body (peripheral nervous system).

For most people, falling asleep and staying asleep are parts of a natural process. Good sleepers are likely to have developed certain lifestyle and dietary habits that promote sound sleep. These habits or behaviors, known as sleep hygiene, can have positive effects on sleep before, during, and after time spent in bed. For other people, particularly those suffering from a sleep disorder, problems falling asleep and staying asleep have a large negative impact on their lives.

Sleep disorders (SDs) are diagnosed and treated by many different healthcare providers, including general practitioners and specialists in neurology, pulmonary medicine, psychiatry, psychology, pediatrics and other fields. The International Classification of Sleep Disorders (ICSD) has over seventy sleep disorders listed, and includes, THE DYSSOMNIAS: Intrinsic Sleep Disorders (Psychophysiological Insomnia, Sleep State Misperception, Idiopathic Insomnia, Narcolepsy, Recurrent Hypersomnia (excessive sleepiness), Idiopathic Hypersomnia, Posttraumatic Hypersomnia, Obstructive Sleep Apnea Syndrome, Central Sleep Apnea Syndrome, Central Alveolar Hypoventilation, Periodic Limb Movement Disorder (PLM), Restless Leg Syndrome (RLS), and Intrinsic Sleep Disorder Not Otherwise Specified (NOS)), Extrinsic Sleep Disorders (Inadequate Sleep Hygiene, Environmental Sleep Disorder, Altitude Insomnia, Adjustment Sleep Disorder, Insufficient Sleep Syndrome, Limit-Setting Sleep Disorder, Sleep-Onset Association Disorder, Food Allergy Insomnia, Nocturnal Eating/Drinking Syndrome, Hypnotic-Dependent Sleep Disorder, Stimulant-Dependent Sleep Disorder, Alcohol-Dependent Sleep Disorder, Toxin-Induced Sleep Disorder, and Extrinsic Sleep Disorder Not Otherwise Specified (NOS)), Circadian Rhythm Sleep Disorders (Time-Zone Change (Jet-Lag), Syndrome Shift-Work Sleep Disorder, Irregular Sleep/Wake Pattern, Delayed Sleep-Phase Syndrome, Advanced Sleep-Phase Syndrome, Non-24-Hour Sleep/Wake Disorder, and Circadian Rhythm Sleep Disorder Not Otherwise Specified (NOS)); and THE PARASOMNIAS: Sleep/Wake Transition Disorders (Rhythmic Movement Disorder, Sleep Starts (Hypnic Jerks), Sleep Talking, and Nocturnal Leg Cramps (Nocturnal Myoclonus), Arousal Disorders (Confusional Awakenings (Sleep Drunkenness), Sleepwalking (Somnambulism), and Night Terrors (Pavor Nocturnus, Incubus Attacks)), Parasomnias Usually Associated With REM Sleep (Nightmares Sleep Paralysis, Impaired Sleep-Related Penile Erections, Sleep-Related Painful Erections, REM Sleep-Related Sinus Arrest, and REM Sleep Behavior Disorder), Other Parasomnias (Sleep Bruxism (Teeth Grinding), Sleep Enuresis (Bed Wetting), Sleep-Related Abnormal Swallowing Syndrome, Nocturnal Paroxysmal Dystonia, Sudden Unexplained Nocturnal Death Syndrome, Primary Snoring Infant Sleep Apnea, Congenital Central Hypoventilation Syndrome, Sudden Infant Death Syndrome (SIDS), Benign Neonatal Sleep Myoclonus, and other Parasomnias Not Otherwise Specified (NOS)). Sleep disorders (SDs) can lead to lowered quality of life and reduced personal health. They endanger public safety by contributing to traffic and industrial accidents. These disorders can lead to problems falling asleep and staying asleep, difficulties staying awake or staying with a regular sleep/wake cycle, sleepwalking, bedwetting, nightmares, and other problems that interfere with sleep. Some sleep disorders can be life-threatening.

There are many limitations to the use of sleeping pills. While pills may help, for example, to aid sleeping during an overnight airplane ride or in a crisis situation to prevent an acute sleeping problem from turning into chronic insomnia, in general, the long-term use of sleeping pills has more risks than benefits. Today, most insomnia patients are not given sleeping pills, and most insomnia patients who do take drugs use them only briefly. Instead, long-term users usually have either a generalized anxiety disorder or a chronic physical illness exacerbated by anxiety, such as arthritis or heart disease.

The drugs used to induce drowsiness (hypnotics and sedatives) are often the same as those used to relieve anxiety (anxiolytics). Today, the most popular anxiety relievers and sleep inducers are the benzodiazepines, which enhance the effect of the inhibitory neurotransmitter gamma-aminobutyric acid (GABA). The benzodiazepines used as sleeping pills include diazepam (VALIUM) and temazepam (RESTORIL). However, development of tolerance to their effects often renders these drugs ineffective within a few weeks. Zolpidem (AMBIEN) is a short-acting drug that is not a benzodiazepine but has a similar mechanism of action. Preparations containing antihistamines are sold over the counter under such names as NYTOL and SOMINEX. They are fairly safe and may be useful, but tolerance may develop quickly. For depression associated with disturbed sleep, sedative antidepressant drugs such as amitriptyline (ELAVIL) and trazodone (DESYREL), are often prescribed. Antipsychotic drugs (neuroleptics) may provoke sleep in anxious, hallucinating manic or schizophrenic patients. Dopaminergic agents such as levadopa/carbidopa, bromocriptine mesylate (PARLODEL, a $D_2$ receptor agonist), and pergolide (a $D_1/D_2$ receptor agonist) have been suggested for use in sleep disorders such as restless leg syndrome (RLS). Opioids such as codeine, propoxyphene, oxycodone, pentazocrine, hydrocodone, and methadone have also been prescribed for patients with severe and relentless symptoms of RLS. However, these drugs are also unfortunately frequently associated with undesirable side effects. The opioids can be addictive and are generally not prescribed for people with a history of addictive behavior. Many people on levodopa therapy may experience what is known as an "augmentation" effect: symptoms begin to occur and intensify during the afternoon or early evening, even though relief is felt at night.

Thus, there is a need for a drug treatment which improves sleep in individuals suffering from sleep disorders and other conditions which interfere with normal sleep that does not exhibit undue side effects.

SUMMARY OF THE INVENTION

According to a broad aspect, the present invention provides a method of improving sleep in an individual in need of such treatment comprising administering to the individual a NO-mimetic in an amount therapeutically effective to improve sleep. The NO-mimetic can be administered to an individual to treat a diagnosed sleep disorder, preferably a dyssomnia. The NO-mimetic can also be administered to improve sleep in an individual suffering from a condition such as fibromyalgia or a peripheral sensory neurogenic syndrome such as restless leg syndrome or diabetic neuropathy, wherein normal sleep is interrupted or interfered with. In a preferred embodiment, the NO-mimetic is administered at an amount therapeutically effective to improve sleep, but ineffective to appreciably alter systemic vascular tone in the individual. Thus, in this present invention, preferred amounts of NO-mimetic therapeutically effective to improve sleep are less than an amount effective to induce systemic vascular dilation or used to manage the symptoms associated with angina pectoris or congestive heart failure. Preferably, a NO-mimetic is administered in an amount between about one half ($\frac{1}{2}$) to about one fortieth ($\frac{1}{40}$) the amount effective to appreciably alter systemic vascular tone in the individual, about one fourth ($\frac{1}{4}$) to about one fortieth ($\frac{1}{40}$) the amount effective to appreciably alter systemic vascular tone in the individual, or one eighth (1/8) to about one fortieth ($\frac{1}{40}$) the amount effective to appreciably alter systemic vascular tone in the individual.

The NO-mimetic can be administered by oral, supralingual, sublingual, transdermal or buccal administration. In a preferred embodiment, the NO-mimetic is administered by transdermal patch.

DETAILED DESCRIPTION OF THE INVENTION

The symptoms in an individual with a sleep disorder or a condition which leads to interrupted sleep manifest themselves through an individual's sensory perception and result from what is believed to be a common underlying neurogenic pathway. It is believed that the inability to sleep experienced by those individuals suffering from sleep disorders and/or conditions which interfere with sleep may be linked to changes in the nitric oxide-cyclic GMP signaling mechanisms within the peripheral and central nervous system as well nitric oxide mechanisms which are independent of cyclic GMP. Further, it is believed that the some symptoms of sleep disorders or other sleep interfering condition are brought on when the neuronal environment or functioning is altered such that cyclic GMP levels are decreased. Nitric oxide is known to signal cGMP in the peripheral nerves (Aoki E. et al. Brain Res. 1993; 620:142–145). It has now been found that NO-mimetics improve sleep via, what is believed to be, action of the NO-mimetic on cyclic GMP dependent pathway and/or pathways independent of cyclic GMP.

The present invention relates to methods for improving sleep in individuals suffering from a sleep disorder or other condition which interferes with or interrupts sleep via administration of a NO-mimetic administered either alone or in combination with additional NO-mimetics or an established drug for sleep disorders. When the NO-mimetic is administered in combination with an established drug for sleep disorders, it is expected that lower doses of the established drug than normally recommended can be used to improve sleep, thereby eliminating many of the unwanted side effects which have been reported for these known treatments. Accordingly, the present invention also provides methods for decreasing the therapeutic dosage of an established drug for sleep disorders or a condition wherein normal sleep is interrupted or interfered with by co-administering the established drug with a NO-mimetic. By co-administer it is meant that the established drug is administered at the same time, just prior to, or just after administration of a NO-mimetic. In one embodiment of the present invention, a single pharmaceutical composition is provided which comprises an established drug for sleep disorders and conditions wherein normal sleep is interrupted or interfered with and a NO-mimetic. Well known methods for formulation such as those described herein can be used to prepares these pharmaceutical compositions. Examples of established drugs for sleep disorders and conditions wherein normal sleep is interrupted or interfered with which can be used in the methods and pharmaceutical compositions of the present invention include, but are not limited to, hypnotics, sedatives and anxiolytics such as the benzodiazepines diazepam and temazepam, zoldipem, antihistamines such as NYTOL and SOMINEX, sedative antidepressants such as amitriptyline and trazodone, dopaminergic agents such as levodopa/carbidopa, bromocriptine mesylate and pergolide, and opioids such as codeine, propoxyphene, oxycodone, pentazocrine, hydrocodone, and methadone.

The methods and compositions are believed to provide relief to an individual suffering from a sleep disorder or a condition which interferes with normal sleep by replacing the deficit in endogenous NO and/or enhancing endogenous neuronal pathways for generating NO or cyclic GMP. Unlike agents currently used to induce sleep such as the sedative hypnotics, the present invention improves sleep by conditioning the neuronal micro-environment in an individual such that their ability to get to sleep and maintain a restful sleep is greatly enhanced. Small, regulatory doses of a NO-mimetic such as nitroglycerin to a patient with a sleep disorder or a condition which leads to interrupted sleep have now been demonstrated to be sufficient to restore the levels of nitric oxide in the nerves to normal levels and decrease the patient's perception of his or her sleep disorder symptoms. The net effect of the NO-mimetic agents which can be used to improve sleep in individuals with sleep disorders or other conditions which interfere with sleep is to act as neuronal conditioners which either directly or indirectly inhibit the action of nerves responsible for generating the characteristic set of symptoms of sleeplessness. While experiments described herein involve use of the NO-mimetic nitroglycerin, it is believed that any NO-mimetic that can alter the action of these nerves can be used to improve sleep in individuals suffering from sleep disorders or other conditions which interfere with sleep. Administration of any NO-mimetic, either alone or in combination with another NO-mimetic or an established drug for treatment of sleep disorders, provides relief of sleeplessness associated with sleep disorders and other conditions wherein sleep is interrupted by maintaining normalized physiological functioning in the nerves responsible for the sleeplessness. As a result, administration of a NO-mimetic prevents the symptoms of the sleep disorder or other condition which interferes with sleep, and is useful in treating sleeplessness associated with sleep disorders and other conditions which interfere with sleep and preventing individuals suffering from such disorders or conditions from perceiving sleep disorder symptoms. Also, unlike agents currently used in the treatment of sleep disorders, the use of low doses of a NO-mimetic are not habit forming or addictive and possibly leave the user feeling more alert upon waking. When the NO-mimetic is used in combination with an established drug for sleep disorders, it is believed that lower doses of the established drug than routinely prescribed can be used, thus alleviating the unwanted habit forming or addictive side effects as well as the lack of alertness upon waking associated with many of these established drugs. Accordingly, pharmaceutical compositions of the present invention which comprise a NO-mimetic and an established drug for sleep disorders and conditions wherein normal sleep is interrupted or interfered with may comprise a lower amount of established drug than routinely prescribed or administered.

The contents of all documents cited in this application are incorporated herein by reference in their entirety.

Definitions:

As used herein in the detailed description and in the claims, the term "sleep disorder (SD)" is intended to mean any irregularity in sleep and is inclusive of diagnosed sleep disorders as well as conditions which interrupt or interfere with normal sleep. Sleep disorders can be acute or chronic. Sleep disorders can also vary in nature and degree. Sleep disorder is also meant to include any new or existing sleep disorders in the two major sleep disorder classes as listed by the International Classification of Sleep Disorders (ICSD) including dyssomnias (insomnia) and parasomnias (abnormal behaviors during sleep). As used herein and in the claims, this term is also meant to be inclusive of conditions which are known to interfere with sleep such as fibromyalgia and peripheral sensory neurogenic syndromes such as restless leg syndrome and diabetic neuropathy. Sleep consists of two distinct states: REM (rapid eye movement) sleep and NREM (non-REM) sleep. Dreaming occurs mostly in REM sleep. Sleep is a cyclic phenomenon, with four or five REM periods during the night, which accounts for about 25 percent of the total night's sleep. Any physical or perceived symptoms which interfere with this cyclic pattern is considered for purposes of the present invention a "sleep disorder" or "condition wherein normal sleep is interrupted or interfered with".

As used herein, the term "insomnia" is intended to mean the sense of not getting enough sleep to awake refreshed and affects 20 to 40 percent of all adults in the course of any year. This term is employed ubiquitously to indicate any and all gradations and types of sleep loss. Although insomnia has myriad causes, it can roughly be divided into three categories: predisposing, precipitating and perpetuating.

Predisposing factors are the built-in characteristics of a person that make him or her vulnerable. Tense or driven people whose heads are brimming with plans or worries can easily lose sleep. Others with severe depression often cannot sleep through the night. In manic disorders, sleeplessness may be important early sign of impending mania in bipolar patients. Predisposing factors also include neurologic conditions such as peripheral sensory neurogenic syndrome or fibromyalgia has also been associated with insomnia. In fact, the peripheral sensory neurogenic syndrome, referred to as restless legs syndrome, is included in the list of dyssomnias published in the International Classification of Sleep Disorders and affects individuals mainly at night as does the involuntary twitching of leg muscles referred to nocturnal myoclonus.

The term "peripheral sensory neurogenic syndrome (PSNS)" refers to the manifestation of a characteristic set of signs and symptoms which result from a common underlying neurogenic pathway. The syndrome is characterized by a number of sensory nerve symptoms including sensations which are described by the patient as pulling, drawing, crawling, tingling, prickly, and sometimes momentarily painful. These sensations typically begin in the toes and legs, but can spread to the hands, arms and trunk. Two of the most commonly observed conditions involving PSNS are the so-called "restless leg syndrome" (also sometimes referred to as "Ekbom's Syndrome") and the sensations in the extremities which accompany diabetic neuropathy. Fibromyalgia or fibrositis is intended to mean a condition that is associated with widespread aching, stiffness and fatigue which originates in the muscles and soft tissues. Fibromyalgia can also include overlapping conditions such as rheumatic pain modulation disorder, myofascial pain syndrome, chronic fatigue syndrome (Buchwald D. Rheum Dis Clin North Am 22(2):219–243, 1996) and sleep-related myoclonus. The cause of fibromyalgia is unknown, but there is evidence to suggest that there is a link between fibromyalgia and sleep disorders since most patients have disrupted sleep patterns (Harding, S. M. Am J Med Sci 315: 367–376, 1998). Methods of the present invention are particularly useful in improving sleep in individuals suffering from conditions such as these which interfere with or interrupt normal sleep.

Precipitating factors are events in life that trigger a period of disturbed sleep. Stresses that precipitate insomnia may include an increase in responsibilities, the loss of a loved one, hospitalization or acute pain, to name a few. An abrupt alteration of schedule, resulting from a change of shift at work or jet lag, can also provoke insomnia.

Perpetuating factors are behaviors that help to maintain sleeplessness once it has begun. These include irregular sleep habits and the use of drugs. Abuse of alcohol may cause or be secondary to the sleep disturbance. Heavy smoking (more than a pack a day) causes difficulty in falling asleep. Short-term or transient insomnia is seen in people who have no history of sleep disturbances and who have a fairly obvious precipitating factor.

As used herein, the term "improve" with respect to sleep, is meant to reduce, prevent (e.g., prophylaxis), reverse (e.g., alleviate), ameliorate, control, or manage the sleeplessness and other symptoms associated with sleep disorders as well as other conditions which interfere with normal sleep. As used herein, "other symptoms" refers to characteristic sensations which result from a common underlying sensory neurogenic pathway and that are associated with sleep disorders, including, for example, dyssomnias (insomnia) and parasomnias (abnormal behaviors during sleep). Improvement of sleep can be measured both quantitatively and qualitatively. For example, qualitatively, sleep improvement can be determined by any number of factors including but not limited to, an easier time falling asleep at bedtime, a decrease in the frequency of waking up in the middle of the night, waking up at an appropriate time (i.e. not too early in the morning), and getting good quality sleep that enables the individual to feel refreshed the following day. Factors which can be used to determine improvement in sleep quantitatively include, but are not limited to, polysomnographic data demonstrating increased sleep efficiency, more time spent asleep in deeper stages of sleep such as Stage 2–4 as opposed to Stage 1, and decreased number of periodic limb movements.

As used herein, the term "apnea" is intended to mean the absence of breathing. During sleep, our breathing changes with the stage or depth of sleep. Some individuals stop breathing for brief intervals, however, when these episodes of apnea become more frequent and last longer, they can cause the body's oxygen level to decrease, which can disrupt sleep. The patient may not fully awaken, but is aroused from the deep restful stages of sleep, and thus feels tired the next day. There are two main types of sleep apnea which may occur together. The most common is obstructive sleep apnea, during which, breathing is blocked by a temporary obstruction of the main airway, usually in the back of the throat. This often occurs because the tongue and throat muscles relax, causing the main airway to close. The muscles of the chest and diaphragm continue to make breathing efforts, but the obstruction prevents any airflow. After a short interval lasting seconds to minutes, the oxygen level drops, causing breathing efforts to become more vigorous, which eventually opens the obstruction and allows airflow to resume. This often occurs with a loud snort and jerking of the body, causing the patient to arouse from deep sleep. After a few breaths, the oxygen level returns to normal, the patient falls back to sleep, the muscles of the main airway relax and the obstruction occurs again. This cycle is then repeated over and over during certain stages of sleep. Most people with obstructive sleep apnea snore suggesting that their main airway is already partly obstructed during sleep, but not all people who snore have obstructive sleep apnea. A less common form of sleep apnea is central sleep apnea, so named because the central control of breathing is abnormal. This control center lies in the brain, and its function can be disrupted by a variety of factors. There is no obstruction to airflow. The patient with sleep apnea stops breathing because the brain suddenly fails to signal the muscles of the chest and diaphragm to keep breathing. These patients do not resume breathing with a snort and body jerk, but merely start and stop breathing at various intervals. Although the mechanism is different than obstructive sleep apnea, sleep is still disturbed by the periodic decreases in oxygen, and the patients suffer from the same daytime symptoms. Some patients may suffer from a combination of the two causes of apnea, a disorder which is called mixed-sleep apnea. Sleep apnea should be suspected in individuals who are noted to have excessive daytime sleepiness and other symptoms described above, especially if they are known to snore and have a restless sleep. Commonly, these patients have exhibited loud snoring for many years, more often are male, and note that the daytime sleepiness has become a progressive problem over many months. Less commonly, they may be bothered by bedwetting or impotence. The sleep problems are often aggravated by alcohol or sedative medications. They are also more readily noticed by the patient's family and friends, especially the bed partner.

As used herein, by the term "NO" or "nitric oxide" it is meant to be inclusive of NO in its various redox forms. The presence of nitric oxide (NO) in biological systems is usually inferred based on its physiological effect. However, several different redox forms of NO such as the NO free radical (NO•), the nitrosonium cation (NO+), the nitroxyl anion (NO−) or other oxides of nitrogen (NOx) are known to exist under physiological conditions and there is no clear evidence to suggest that one form is favored over another (Butler et al. Trends Pharmacol. Sci. 16:18–22 (1995); Stamler et al. Science 258:1898–1902 (1992)). NO is also know to react with thiols to form S-nitrosothiols (RS-NO) and may represent a long-term storage form for NO. Thus, the term "NO" as used herein refers to any and all forms of nitric oxide which exist under physiological conditions.

As used herein, the term "NO-mimetic" is intended to mean NO (nitric oxide), or a functional equivalent thereof; any compound which mimics the effects of NO, generates or releases NO through biotransformation, any compound which generates NO spontaneously, any compound which spontaneously releases NO, or any compound which in any other manner generates NO or a NO-like moiety when administered to a mammal. Such a compound can also be referred to as a "NO donor", "NO prodrug", "NO producing agent", "NO delivering compound", "NO generating agent" and "NO provider". Examples of such compounds include, but are not necessarily limited to: metabolic precursors for NO such as L-arginine and L-citrulline; so-called "organo-nitrates" such as nitroglycerin (GTN), isosorbide 5-mononitrate (ISMN), isosorbide dinitrate (ISDN) pentaerythritol tetranitrate (PETN), erythrityl tetranitrate (ETN), amino acid derivatives such as N-hydroxy-L-arginine (NOHA), $N^6$-(1-iminoethyl)lysine) (L-NIL), L-$N^5$-(1-iminoethyl)ornithine (LN-NIO), $N^a$-methyl-L-arginine (L-NMMA), and S-nitrosoglutathione (SNOG); other compounds which generate or release NO under physiologic conditions such as S,S-dinitrosodithiol (SSDD), [N-[2-(nitroxyethyl)]-3-pyridinecarboxamide (nicorandil), sodium nitroprusside (SNP), S-nitroso-N-acetylpenicillamine (SNAP), 3-morpholino-sydnonimine (SIN-1), molsidomine, DEA-NONOate (2-(N,N-diethylamino)-diazenolate-2-oxide), spermine NONOate (N-[4-[1-(3-aminopropyl)-2-hydroxy-2-nitrosohydrazino]butyl-1,3-propanediamine), and NO gas, or a functional equivalent thereof. The organic nitrates GTN, ISMN, ISDN, ETN, and PETN, as well as nicorandil are commercially available in pharmaceutical dosage forms (see Tables 3 and 4). SIN-1, SNAP, S-thioglutathione, L-NMMA, L-NIL, L-NIO, spermine NONOate, and DEA-NONOate are commercially available from Biotium, Inc. 183 Shoreline Court, Richmond, Calif., USA. The term "NO-mimetic", as used herein, is also intended to mean any compound that acts as a NO pathway mimetic, that has NO-like activity, or that mimics the effect of NO, e.g. CO. Such compounds do not necessarily release, generate, or provide NO, but they have the same effect as NO on a pathway that is affected by NO. For example, NO can have both cyclic GMP-dependent and cyclic GMP-independent effects. NO is known to activate the soluble form of guanylyl cyclase thereby increasing intracellular levels of the second messenger cyclic GMP. As such, any compounds which directly activate guanylyl cyclase such as 3-(5'-hydroxymethyl-2'furyl)-1-benzyl indazole (YC-1) or which act as cyclic-GMP analogues such as 8-bromo-cyclic-GMP (8-Br-cGMP) and 8-(4-chlorophenylthio)guanosine 3',5'-cyclic monophosphate (8-PCPT-cGMP) are considered NO-mimetics. For purposes of the present invention, phosphodiesterase inhibitors or any compound that inhibits enzymatic degradation of a cyclic nucleotide are also considered NO-mimetics. These NO-mimetics include, for example, compounds that antagonize or inhibit the biosynthesis or actions of any enzyme that degrades a cyclic nucleotide. Such degradation may comprise the cleavage of a phosphodiester such as cGMP or cAMP to give a phosphomonoester and a free hydroxyl group. Examples of these NO-mimetics include, but are not limited to, sildenafil; cilostamide (N-cyclohexyl-N-methyl-4-(1,2-dihydro-2-oxo-6-quinolyloxy)butyramide; dipyridamole (2,6-bis (diethanol-amino)-4,8-dipipendinopyrimido-[5,4-d] pyrimidine); erythro-9-(2-hydroxy-3-nonyl)adenine (EHNA); etazolate (1-ethyl-4-[(1-methylethylidene) hydrazino]-1H-pyrazolo-[3,4-b]-pyridine-5-carboxylic acid, ethyl ester); 4-[[3,4-(methylene-dioxy)benzyl]amino]-6-chloroquinazoline (MBCQ); 8-methoxymethyl-1-methyl-3-(2-methylpropyl)xanthine (MMPX); 1-(3- chlorophenylamino)-4-phenyl-phthalazine (MY-5445); 4-(3-butoxy-4-methoxyphenyl)methyl-2-imidazolidone (Ro 20-1724); Rolipram (4-(3-(cyclopentyloxy)-4-methoxyphenyl)pyrrolidin-2-one); vinpocetine (3a,16a)-eburnamenine-14-carboxylic acid ethyl ester); zaprinast (2-propyloxyphenyl)-8-azapurin-6-one); and zardaverine (6-[4-(difluoro-methoxy)-3-methoxyphenyl]-3(2H)-pyridazinone. These NO-mimetics are available from Tocris Cookson Inc., 114 Holloway Road, Suite 200 Ballwin, Mo. 63011 USA.

Also contemplated as falling within the scope of the present invention for use in improving sleep are the pharmaceutically acceptable salts of any of the foregoing NO-mimetics. As used herein, the term "pharmaceutically acceptable salt" refers to those salts which are within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1–19 (1977). The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalene-sulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Preferred acid addition salts of compounds contemplated for use in the method of the present invention are the hydrochloride and acetate salts.

The term "prodrug" refers to compounds that are rapidly transformed in vivo to yield NO, as for example, by hydrolysis in blood or other biotransformation mechanism. T. Higuchi and V. Stella provide a thorough discussion of the prodrug concept in "Prodrugs as Novel Delivery Systems," Vol. 14 of the A.C.S. Symposium Series, American Chemical Society (1975). Examples of esters useful as prodrugs for compounds containing carboxyl groups may be found on pages 14–21 of *Bioreversible Carriers in Drug Design: Theory and Application*, edited by E. B. Roche, Pergamon Press (1987).

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The phrase "without appreciably altering systemic vascular tone" as used herein means not affecting mean arterial pressure so as to produce inappropriate systemic vasodilation with effects such as hypotension, headache, and flushing.

Pharmaceutical Formulations:

Pharmaceutical formulations for the administration of NO-mimetics to improve sleep in accordance with the method of the present invention may take the form of ointments, transdermal patches, transbuccal patches, injectables, nasal inhalant forms, spray forms for deep lung delivery through the mouth, orally administered ingestable tablets and capsules, and tablets or lozenges, or "lollipop" formulations for administration through the oral mucosal tissue. The latter formulations include tablets, lozenges and the like which are dissolved while being held on or under the tongue, or in the buccal pouch. It is preferred that the pharmaceutical preparations provide the desired dosage over a sustained period of time selected based upon the individual needs of a patient suffering from a sleep disorder or other condition which interferes with or interrupts normal sleep. Thus, for purposes of the present invention, a "sustained period" may range from only a few minutes up to about 12 hours and is inclusive of, but not limited to intermediary ranges such as 0.5–10, 2–8, 2–6 and 3–4 hours.

The pharmaceutical compositions of the present invention comprise a therapeutically effective amount of a NO-mimetic formulated together with one or more pharmaceutically acceptable carriers. In addition to the NO-mimetic, the pharmaceutical compositions of the present invention may further comprise an established durg for sleep disorders and conditions wherein normal sleep is interrupted or interfered with. Examples of established drugs for use in these pharmaceutical compositions include, but are not limited to, hypnotics, sedatives and anxiolytics such as the benzodiazepines diazepam and temazepam, zoldipem, antihistamines such as NYTOL and SOMINEX, sedative antidepressants such as amitriptyline and trazodone, dopaminergic agents such as levodopa/carbidopa, bromocriptine mesylate and pergolide, and opioids such as codeine, propoxyphene, oxycodone, pentazocrine, hydrocodone, and methadone.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to an individual orally, rectally, parenterally, intracisternally, intravaginally, intraperitoneally, topically (as by powders, ointments, or drops), supralingually (on the tongue) sublingually (under the tongue), bucally (held in the buccal pouch), or as an oral or nasal spray. The oral spray may be in the form of a powder or mist which is delivered to the deep lungs by oral inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In cases where it is desirable to prolong the effect of the drug, the absorption of the drug from subcutaneous or intramuscular injection can be slowed. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and I) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like. The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention. Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

A preferred mode of delivery is one which provides a reasonably steady-state delivery of therapeutic agent, so as to maintain steady-state plasma concentrations. Such delivery avoids any substantial initial spike in plasma concentration of the agent, as it would be desirable to avoid plasma concentrations that produce negative side effects. Transdermal patches and pulsed delivery systems are preferred modes of delivery.

Nitroglycerin Transdermal Patches:

A preferred formulation and dose delivery system of the present invention comprises a patch for transdermal delivery of a NO-mimetic such as nitroglycerin, isosorbide 5-mononitrate, isosorbide dinitrate, pentaerythritol tetranitrate, and erythrityl tetranitrate. A preferred NO-mimetic for transdermal patches in accordance with the present invention is nitroglycerin.

Transdermal nitroglycerin patches (MINITRAN, 3M Corporation, St. Paul, Minn., USA) were prepared in three sizes, both in forms containing nitroglycerin and drug-free placebo. The patches had a release liner, uniformly of 1 inch$^2$ (6.65 cm$^2$), with a circular drug-containing (or placebo) patch having areas of 3.33 cm$^2$, 1.65 cm$^2$, or 0.825 cm$^2$. The various-size drug-containing patches had nitroglycerin loadings of about 2.7 mg of nitroglycerin/cm$^2$ and the total loadings shown in Table 1.

3M MINITRAN transdermal nitroglycerin patches of 10 cm$^2$ and 20 cm$^2$ areas deliver plasma levels of 102 pg/mL and between 129 pg/mL and 310 pg/mL, respectively. The 3.3 cm$^2$ patch, with a total loading of 9 mg of nitroglycerin in each patch, has a mean rate of drug delivery of about 0.81 mg/cm$^2$/hour. The two smaller patches (1.65 cm$^2$ and 0.825 cm$^2$) used in the studies described herein had areas of one half and one fourth the 3.33 cm$^2$ patch. Based on the ratios of patch surface area and assuming linearity in the rates of drug delivery, the estimated rates of delivery and extrapolated values of plasma levels of nitroglycerin for the three low or microdose patches are given in Table 1.

TABLE 1

Calculated Delivery Rates and Plasma Levels of Nitroglycerin Delivered from Microdose Patches

| Patch Area (cm$^2$) | Delivery Rate mg/cm$^2$/24 hours | Plasma Level (pg/mL) |
|---|---|---|
| 10.0 | 0.81 | 102[1] |
| 3.33 | 0.63–0.81[2] | 34[3] |
| 1.65 | 0.63–0.81[2] | 17[3] |
| 0.825 | 0.63–0.81[2] | 9[3] |

[1]Measured; [2]Estimated; [3]Extrapolated from larger-size patches assuming linearity.

The stability of low or microdose transdermal nitroglycerin patches for use in accordance with the method of the present invention is illustrated by the data appearing in Table 2.

TABLE 2

Nitroglycerin Patch Stability

Nitroglycerin content (mg/patch)

| Lot | Patch Size (cm$^2$) | Theoretical | Initial | After 6 months storage at 25° C. and 60% relative humidity | After 6 months storage at 70° C. and 60% relative humidity |
|---|---|---|---|---|---|
| A | 3.33 | 9.0 | 9.22 | 9.24 | 9.03 |
| B | 1.65 | 4.5 | 4.63 | 4.72 | 4.45 |
| C | 0.825 | 2.25 | 2.33 | 2.28 | 2.17 |

Dosing and Administration:

In doses used for prophylaxis of acute attacks of angina pectoris and for general vasodilation, compounds which generate or release NO, such as those listed above, dilate the capacitance veins and the conductance arteries. Dilation of the capacitance veins decreases the ventricular filling pressure, while dilation of the conductance arteries decreases arterial impedance. The former effect tends to decrease cardiac output, while the latter tends to increase it with a net increase in cardiac output if serum levels of NO are maintained.

These compounds all have a common mechanism of action which involves in vivo denitration to produce NO which is also an endothelial-derived relaxing factor (EDRF) endogenously generated by the oxidation of L-arginine. NO reacts with sulfhydryl compounds in blood vessels to form adducts which stimulate guanylyl cyclase, causing smooth muscle relaxation.

In accordance with the present invention, a NO-mimetic is administered to an individual in an amount therapeutically effective to improve sleep. An effective amount can be that which is provided to induce systemic vasodilation in normal circulation in an individual. Therapeutically effective amounts of NO-mimetics that induce systemic vasodilation in normal circulation in a human are given in Table 3 under the column heading "Commercial Product". However, administration of such amounts of NO-mimetics is often associated with negative side effects of the NO-mimetics. It has been discovered in the present invention that sleep can be improved in individuals with sleep disorders by the administration of a NO-mimetic in an amount substantially smaller than that which appreciably alters systemic tone in a human or is used to manage the symptoms associated with angina or congestive heart failure, thereby largely avoiding the negative side effects of NO-mimetics. Thus, in accordance with a preferred aspect of the invention, typical "low doses" of NO-mimetics are as described in Table 3 under the column heading "Preferred Dose According to the Present Invention".

The terms "low dose" or "microdose" of a NO-mimetic are used interchangeably throughout this specification and the appended claims and mean a dose which ranges between about one half (½) to about one fortieth (1/40) of the dose known to appreciably alter systemic vascular tone in normal circulation in a human. This "low" or "microdose" range for the use of NO-mimetics in the present invention is derived from the observation that doses of a NO-mimetic which are below the upper end of the range, i.e. below about ½ the normal dose, systemic vasodilation is generally no longer seen. Doses below the low end of the range, i.e. below about 1/40 the normal dose, do not elicit the desired improvement in sleep. Accordingly, one of skill in the art can routinely select and/or determine appropriate doses of an NO-mimetic to be administered in the present invention to improve sleep based upon the teachings provided herein and upon doses of NO-mimetics established in the prior art to appreciably alter systemic vascular tone. Appropriate doses to be administered to an individual may be routinely selected based upon the teachings herein by monitoring the patient for symptoms of inappropriate systemic vasodilation such as hypotension, headache, and flushing as well as parameters as set forth herein for determining improved sleep. Appropriate doses will improve one or more parameters of sleep as set forth herein. For examples of typical preferred low-dose or microdose ranges for representative NO-mimetics, see Table 3.

TABLE 3

Typical Vasodilatory and Microdoses of Organonitrates

| Compound | Commercial Product | Vasodilatory Dose | Preferred Dose According to the Present Invention |
|---|---|---|---|
| Nitroglycerin (sublingual tablets) | NITROSTAT(Parke-Davis); 0.3 mg, 0.4 mg and 0.6 mg sublingual tablets | Dissolve one tablet (0.3–0.6 mg) sublingually or in the buccal pouch at the first sign of an acute anginal attack | Dissolve one tablet containing from about 0.02 to about 0.1 mg sublingually or in the buccal pouch as needed |
| Nitroglycerin (lingual aerosol) | NITROLINGUAL Spray (Rhone-Poulenc Rorer); metered aerosol, 0.4 mg/metered dose | One or two metered doses (0.4–0.8 mg) sprayed onto or under the tongue at the onset of an anginal attack | About 0.02 mg to about 0.1 mg sprayed onto or under the tongue as needed |
| Nitroglycerin (transdermal patch) | MINITRAN (3M Corporation) ; Transdermal patches having the following characteristics (size (cm$^2$), delivery rate (mg/h)); (3.3, 0.1; 6.7, 0.2; 13.3, 0.4; and 20.0, 0.6) | Suggested dose is between 0.2–0.8 mg/h for 12–14 h daily with a minimum nitrate-free interval of 10–12 h | About 0.0125–0.1 mg/h as needed |
| Nitroglycerin (ointment) | NITRO-BID Ointment (Hoechst Marion Roussel); lactose and 2% nitroglycerin in a base of lanolin and white petrolatum. Each inch (2.5 cm), as squeezed from the tube, contains approximately 15 mg of nitroglycerin | Doses used in clinical trials have ranged from ½ inch (1.3 cm; 7.5 mg), to 2 inches (5.1 cm; 30 mg), typically applied to 36 square inches (232 square cm) of skin on the arms or legs | Ointment containing about 0.375 mg to about 3.75 mg of nitroglycerin applied to the arms or legs over an area of about 36 square inches (232 cm$^2$) |
| Isosorbide 5-mononitrate | IMSO (Wyeth-Ayerst) 20 mg tablets | 20 mg twice daily | About 1 to about 2.5 mg twice daily |
| Erythrityl tetranitrate | CARDILATE (Burroughs-Wellcome); oral/sublingual tablets, 5 mg, 10 mg | Chronic (Adults): 10 mg orally 4 times daily, gradually increased to 20 mg, if necessary, not to exceed 100 mg/day. | Chronic (Adults): About 0.5 to about 1.25 mg orally 4 times daily, gradually increased to about 0.5 to about 2.5 mg/day, if necessary, not to exceed about 5 to about 12.5 mg/day |
| Sodium nitroprusside | NIPRIDE (Roche); NITROPRESS (Abbott); intravenous solution | Slow infusion at a rate of 0.5 µg/kg/min of a solution of 50 mg in 500–1000 mL of 5% dextrose up to a limit of 3.5 mg/kg in brief infusions | Slow infusion at a rate of from 0.025 µg/kg/min to about 0.063 µg/kg/min of a solution of 50 mg in 500–1000 mL of 5% dextrose up to a limit of about 0.18 mg/kg to about 0.44 mg/kg in brief infusions |
| Molsidomine | CORVATON (Hoechst Marion Roussel); 2 | 2 mg/day up to 36 mg/day given in | 0.1 mg/day up to 4.5 mg/day given in separate doses either |

TABLE 3-continued

Typical Vasodilatory and Microdoses of Organonitrates

| Compound | Commercial Product | Vasodilatory Dose | Preferred Dose According to the Present Invention |
|---|---|---|---|
| | mg, 4 mg, and 6 mg tablets | separate doses either twice or three times daily | twice or three times daily |
| Nicorandil | NICORANDIL (Chugai Pharmaceuticals, Japan), DANCOR (Merck) 10 mg, 20 mg tablets | For the treatment of angina 10–20 mg twice daily | About 0.5 mg to about 1 mg twice daily |

Using GTN transdermal patches as an example, Table 4 compares the sizes ($cm^2$) patches typically used in accordance with the present invention to the size ($cm^2$) of the smallest patch currently available from 3M (3M MINITRAN patch). As can be seen from Table 4, the sizes of patches used in accordance with the present invention are about ½ to 1/40 the size of the smallest commercially available patch. Assuming that dosage scales linearly with patch size, the patch sizes used in the present invention provide dosages in the range of about ½ to 1/40 those provided by the smallest commercially available patch.

For those formulations containing a NO-mimetic which is commercially available, the low dose or microdose formulations contemplated for use in the method of the present invention are formulated according to the same methods as the commercially available higher dose formulations, but with amounts generally ranging between about ½ and about 1/40 of the active ingredient. Methods of formulation are within the skill of pharmaceutical formulation chemists and are fully described in such works as *Remington's Pharmaceutical Science*, 18th Edition, Alfonso R. Gennaro, Ed., Mack Publishing Co., Easton, Pa., USA, 1990.

TABLE 4

Comparison of 3M and Invention Patch Areas

| 3M Patch Area ($cm^2$) | Invention Patch Areas ($cm^2$) | Invention Patch Areas as a Fraction of 3M Patch Area |
|---|---|---|
| 3.3 | 1.65 | ½ |
| 3.3 | 0.825 or 0.83 | ¼ |
| 3.3 | 0.413 | ⅛ |
| 3.3 | 0.206 | 1/16 |
| 3.3 | 0.165 | 1/20 |
| 3.3 | 0.110 | 1/30 |
| 3.3 | 0.0825 | 1/40 |

As can be seen from the data in Table 4, patches according to the invention providing about ⅛ or less of the dose of GTN known to induce systemic vasodilation are considerably small. When such small doses of NO-mimetic are desired, it is preferable to reformulate (i.e., dilute) the NO-mimetic so that a larger patch size can be used, while maintaining the required low dose. Also, since the laws of mass action are a key factor in determining delivery rates, it has also been contemplated that there is a potential that the rate of drug delivery in the smaller sized patches would not scale linearly (i.e. a patch area of 1/40 as presented in Tables 1 and 4, may deliver plasma levels of the drug at less than 1/40 the dose of the 3.3 $cm^2$ patch). As discussed above, methods of such formulation are within the skill of pharmaceutical formulation chemists and are fully described in such works as *Remington's Pharmaceutical Science*, 18th Edition, Alfonso R. Gennaro, Ed., Mack Publishing Co., Easton, Pa., USA, 1990.

The following nonlimiting examples are provided to further illustrate the present invention.

EXAMPLES

Example 1

Improving Sleep in 4 Subjects with Sleep Disorders
Subject 1:

The subject was a 50 year old male with a history of sleep disorders including PLMS for at least 4 years. Over this period the subject had five visits to a sleep laboratory, which confirmed his diagnosis of PLMS, and through which various treatments were devised. These included drug therapies with PAXIL/WELLBUTRIN, CLOMIPRAMINE, IMOVANE, DESIPPAMINE, ZOLOFT, TEMAZEPAM, TRYPTAN, and FLUVOXAMINE. None of the drug therapies were successful in treating the symptoms of the sleep disorder, and, through lack of restorative sleep and inappropriate drug therapy, the subject's condition gradually deteriorated, leading additionally to depression and overall poor health, such that his career was in jeopardy.

At this point, the subject was administered a 1.65 $cm^2$ GTN patch as described above in reference to Table 4. The patch was applied just before retiring at night. This was repeated for three consecutive nights. The subject reported having a restful night's sleep with substantially no sleep disorder symptoms, and a minor headache that resolved within one hour of waking. On the fourth night, the subject applied a 1.1 $cm^2$ GTN patch, and on the fifth night, a 0.825 $cm^2$ GTN patch. The subject reported that the 0.825 $cm^2$ GTN patch ameliorated the sleep disorder symptoms, and produced no negative side-effects; i.e., no headache.

Subject 2:

The subject was a 43 year old male who has chronically had difficulties sleeping (at least 10 years). The subject has asthma treated only with periodic use of VENTOLIN (1–3 times daily). The subject stated that the major reasons/symptoms for his inability to sleep or not to have a restful sleep appeared to be: (I) inability to stop actively thinking about current or the next day's events (i.e. anxiety, tension, stress, creative thought processes); (ii) an overall restlessness that occurs following late-in-the-day exercise; (iii) a leg restlessness that occurs up to three hours prior to going to bed; and/or (iv) an inability to get to sleep but with no apparent cause. All of these reasons fall under the three categorical causes of insomnia: predisposing, precipitating and perpetuating.

At the onset of any the above described symptoms, the subject used a 0.825 $cm^2$ transdermal GTN patch, initially by dividing it into quarters (0.206 cm$^2$) or halves (0.413 cm$^2$) as described above in reference to Table 4. The GTN-containing patch material was cut with scissors prior to use and the remaining portion kept within the original foil package between uses. During the first week of use, the subject began by applying a quarter of the 0.825 cm$^2$ GTN patch (0.206 cm$^2$) to his skin, while a second quarter of the GTN patch (0.206 cm$^2$) was applied next to the first quarter of the GTN patch if the subject determined that a satisfactory effect had not been obtained. During the initial assessment, the subject found that he had to apply two quarter pieces (2×0.206 cm$^2$) of the 0.825 cm$^2$ GTN patch in about half of the trials meaning that a total GTN patch area of 0.413 cm$^2$ was used. Following this initial assessment, the subject only used half sections (0.413 cm$^2$) of the 0.833 cm$^2$ GTN patch.

In general, in the initial trials, the subject indicated that the time to "response" (meaning a perceived relief of the symptoms that caused the insomnia) was between 20–45 minutes. This was determined by the subject perceiving changes which included: an increased feeling of relaxation, a withdrawal of tension (particularly from the upper body), a feeling within the head similar to the beginning of a very mild headache but without discomfort, and/or decreased irritability in the lower extremities (i.e. reduced leg movements).

In a specific case, the subject had attended a conference in a different city and indicated that the use of half of a 0.825 cm$^2$ GTN patch (0.413 cm$^2$) each evening provided complete relief of the sleep disturbances that are normally greatly exaggerated during stays at hotels when away without his family. This improved sleeping behavior was corroborated by his roommate (a physician) who had observed the sleeping difficulty at numerous other conferences prior to this one.

In another specific case, the subject indicated that during one evening, use of half of a 0.825 cm$^2$ GTN patch (0.413 cm$^2$) had relieved the predisposing symptoms of insomnia and allowed him to fall asleep within a 10–15 minute period. However, the subject awoke 1–1.5 hours later with similar signs and symptoms as had occurred prior to falling asleep. It was at this time that the subject discovered that the half-patch had fallen off. Upon re-applying a new half of a 0.825 cm$^2$ GTN patch (0.413 cm$^2$) the subject was able to return to sleep.

The subject has been using half of a 0.825 cm$^2$ GTN patch (0.413 cm$^2$) for over 8 weeks to aid his sleep. No untoward effects have resulted from the use of half of a 0.825 cm$^2$ GTN patch (0.413 cm$^2$). At the time this data was collected, the subject was using half of a 0.825 cm$^2$ GTN patch (0.413 cm$^2$) 3–4 times each week as required and planned to continue to do so.

Subject 3:

The subject was a 29 year old male who had experienced problems sleeping on numerous occasions following intense, late evening physical activity. On four separate occasions following a two hour session of hockey, as per usual, the subject returned home around midnight feeling invigorated and unable to go to sleep. However, at this point, the subject applied to the skin on the inside of his wrist one-half of a 0.825 cm$^2$ GTN patch (0.413 cm$^2$, as described above in reference to Table 4) and went to bed. Following application of half of a 0.825 cm$^2$ GTN patch (0.413 cm$^2$) the subject reported feeling a calming effect, a decrease in his muscle tension and an improvement in his ability to relax. The subject also reported that the last thing that he remembered before waking up rested and feeling like he had a very restful sleep was placing the patch on his wrist. The subject reported a mild headache upon waking, that was gone within 30 minutes of removing the patch. The subject was continuing to use the GTN patch to facilitate sleeping following late evening exercise at the time this data was collected.

Subject 4:

A thirty-seven year old male, suffering from periodic restless leg syndrome was administered nitroglycerin by transdermal patch in a modified blinded study. The subject was administered either placebo or a nitroglycerin patch having an area of 0.833 cm$^2$ of the type described above. The patches were coded as to whether they represented a placebo patch or a patch containing nitroglycerin. A patch was randomly selected from the lot of patches containing placebo or active patch by the test administrator and applied to the inner wrist of the subject approximately 1 hour to 1.5 hours just prior to retiring at night.

Later in the evening, or on the morning following the application of a transdermal patch, the subject would make an assessment whether he had received a placebo patch or a patch containing nitroglycerin, based upon the extent to which the symptoms had been alleviated. The results are presented in Table 5. If symptoms were present and alleviated, and the subject correctly identified the patch as containing nitroglycerin, the entry for the date in question was scored as "+". Likewise, if symptoms were present, and not alleviated, and the subject correctly identified the patch as placebo, the entry for the date in question was scored as "+". If the subject experienced PSNS symptoms, and incorrectly identified the patch as placebo when it contained nitroglycerin, the entry for the date in question was scored as "−". Similarly, if symptoms were present and not alleviated by a patch containing nitroglycerin, and the subject identified the patch as placebo, a score of "−" was entered for the date in question.

TABLE 5

| Date  | Score |
|-------|-------|
| 10/28 | +     |
| 10/29 | +     |
| 10/31 | +[1]  |
| 11/1  | −     |
| 11/2  | +[1]  |
| 11/3  | −[2]  |
| 11/4  | +     |
| 11/5  | +     |

[1]On these dates the subject, after correctly identifying the patch as placebo, requested a patch containing nitroglycerin; after applying this patch the symptoms disappeared shortly thereafter.
[2]The subject incorrectly identified a nitroglycerin-containing patch as placebo.

Example 2

Phase II Clinical Study

A human clinical trial is currently being conducted at the Toronto Western Hospital, Centre for Sleep and Chronobiology, Sleep Disorders Clinic. The trial is a prospective, randomized, double blind, placebo controlled, single center study. Twenty subjects meeting inclusion and exclusion criteria underwent two identical in-clinic assessments on consecutive evenings; one night on the study medication and the other night on placebo. The study measured standard polysomnographic parameters, blood pressure, and the subject's assessment of his/her sleep quality and RLS/PLMS symptoms.

Inclusion criteria for the study include that the subject must be adult between the ages of 18 and 65, with diagnosed mild or moderate primary RLS and PLMS according to the American Sleep Disorders Association, International Classification of Sleep Disorders, revised: Diagnostic and Coding Manual, Rochester Minn., 1997. Subjects included suffered from the presence of RLS symptoms interfering with sleep onset or the continuity of sleep more than three nights per week for at least 3 months. Subjects included suffered from active RLS/PLMS symptoms during the course of the study.

Diagnostic criteria for RLS included that the subject has a complaint of an unpleasant sensation in the legs at night or difficulty in initiating sleep and disagreeable sensations of "creeping" inside the calves present and often associated with general aches and pains in the legs. Further, this discomfort is relieved by movement of the limbs. Mild RLS is defined as occurring episodically, with no more than a mild disruption of sleep onset that does not cause the subject significant distress. Moderate RLS is defined as occurring less than twice a week, with significant delay of sleep onset, moderate disruption of sleep, and mild impairment of daytime function.

Diagnostic Criteria for PLMS included that the subject has a complaint of insomnia or excessive sleepiness and that the subject occasionally will be asymptomatic, and the movements are noticed by an observer. In addition, repetitive highly stereotyped limb muscle movements are present; in the leg, these movements are characterized by extension of the big toe in combination with partial flexion of the ankle, knee, and sometimes hip. Mild PLMS is defined as mild insomnia or mild sleepiness typically associated with a PLM index of 5 or more but less than 25. Moderate PLMS is defined as moderate insomnia or moderate sleepiness typically associated with a PLM index of 25 or more but less than 50.

Subjects excluded from the study included those currently receiving organic nitrate therapy of any kind; those having received pharmacological treatment for their RLS symptoms within the last 2 weeks; those with co-morbid sleep related conditions such as sleep apnea; those diagnosed neurological conditions such as Parkinson's, multiple sclerosis or Alzheimer's disease; those with known hypersensitivity or idiosyncratic reaction to nitroglycerin or any component of the formulation; those diagnosed with primary psychiatric disorders such as schizophrenia, schizo-affective, bipolar or other major depressive disorder; those diagnosed with diabetic neuropathy, anemia or iron deficiency (serum ferritin levels below 20 $\mu$g/l for men, 10 $\mu$l for women), or chronic renal failure; those known to have abused drugs or alcohol within the past one year; those suffering from open or closed angle glaucoma; those with (treated or untreated) hypertension (supine systolic pressure >160 mmHg or 100 mm Hg at screening); those with hypotension, defined as resting blood pressure <90/50 mmHg; those suffering from uncorrected hypovolemia, myocardial infarction within the previous six months, unstable angina, or any other major active cardiovascular impairment; those having been treated with any investigational therapy or device within the previous month; and those with any clinical condition which in the opinion of the investigator would not allow safe completion of the protocol and safe administration of the trial medication.

Efficacy of treatment was assessed by a reduction in PLMS index; an increase in total sleep time; an increase in sleep efficiency; improvement in sleep latency; subjective assessment of improvement in severity of RLS/PLMS symptoms; and satisfaction with treatment received.

Safety was assessed by monitoring for blood pressure changes, changes in EKG, changes in EOG, EMG, EEG readings, and any other adverse events in treatment versus control.

Nitroglycerin for the treatment of RLS, PLMS and sleep symptoms was provided in single dose transdermal patches packaged in individual foil pouches. Each single dose transdermal patch has a surface area of 0.83 cm$^2$, contains 2.25 mg of nitroglycerin, and releases the nitroglycerin at a rate of 0.025 mg/hour (0.75 mg/cm$^2$/24 hours). After 8 hours 85% of the nitroglycerin remains entrained in the adhesive substrate of the transdermal patch.

Placebo patches were identical in all respects except that they did not contain nitroglycerin.

Results from one subject in this Phase II study are depicted in Table 6 below. This subject spent two consecutive nights in a sleep clinic. The first night no treatment was administered. These second night a transdermal GTN patch was applied 1 hour before retiring to bed.

Blood pressure did not change in this subject following administration of the GTN patch.

TABLE 6

Results from ongoing Phase II study

| | No Treatment | Treatment |
|---|---|---|
| Sleep latency (min) | 26.0 | 16.5 |
| REM latency (min) | 116.0 | 86.5 |
| Sleep Efficiency (%) | 72.4 | 83.7 |
| Stage 1 (min) | 25.0 | 25.0 |
| Stage 2 (min) | 133.0 | 186.5 |
| Stage 3 (min) | 33.5 | 49.5 |
| Stage 4 (min) | 44.5 | 12.5 |
| REM (min) | 53.5 | 64.5 |
| Arousal index (/hr) | 14.7 | 16.3 |
| PLMS index (/hr) | 15.3 | 8.5 |
| PLMS arousals (/hr) | 3.9 | 4.8 |

While there have been shown and described what are believed at present to constitute the preferred embodiments of the present invention, it will be apparent to one of ordinary skill in the art that various modifications may be made therein without departing from the scope of the invention as it is defined by the appended claims.

What is claimed is:

1. A method for improving sleep in an individual suffering from a sleep disorder, said method comprising administering to the individual a NO-mimetic in an amount therapeutically effective to improve sleep in the individual, where the amount of NO-mimetic administered is about one half to about one fortieth of the amount of NO-mimetic known to appreciably alter systemic vascular tone in normal circulation in a human.

2. The method of claim 1 wherein the amount of NO-mimetic administered is less than an amount effective to appreciably alter systemic vascular tone.

3. The method of claim 1, wherein the NO-mimetic is administered by transdermal patch.

4. The method of claim 1 wherein the NO-mimetic is co-administered with an established drug for sleep disorders or a condition wherein sleep is interrupted or interfered with.

5. The method of claim 1 wherein the NO-mimetic is a member selected from the group consisting of an organonitrate, an amino acid derivative and a phosphodiesterase inhibitor.

6. The method of claim 1 wherein said NO-mimetic is a member selected from the group consisting of nitroglycerin (GTN), isoaorbide 5-mononitrate (ISMN), isosorbide dinitrate (ISDN), pentaerythritol tetranitrate (PETN), erythrityl tetranitrate (ETN), N-hydroxy-L-arginine (NOHA), N$^6$-(1-iminoethyl)lysine) (L-NJL), L-N$^5$-(1-iminoethyl)ornithine (LN-NIO), $N^G$-methyl-L-arginine (L-NMMA), and S-nitrosoglutathione (SNOG); S,S-dinitrosodithiol (SSDD), [N-[2-(nitroxyethyl)]-3-pyridinecarboxamide (nicorandil), sodium nitroprusside (SNP), S-nitroso-N-acetylpenicillamine (SNAP), 3-morpholino-sydnonimine (SIN-1), molsidomine, DEA-NONOate (2-(N,N-diethylamino)-diazenolate-2-oxide), spermine NONOate (N-[4-[1-(3-aminopropyl)-2-hydroxy-2-nitrosohydrazino] butyl-1,3-propanediamine), and NO gas.

7. The method of claim 6 wherein said NO-mimetic is nitroglycerin (GTN).

8. The method of claim 1 wherein said NO-mimetic is an activator of guanylyl cyclase selected from the group consisting of 3-(5'-hydroxymethyl-2'furyl)-1-benzyl indazole (YC-1), 8-bromo-cyclic-GMP (8-Br-cGMP), and 8-(4-chlorophenylthio)guanosine 3',5'-cyclic monophosphate (8-PCPT-cGMP).

9. The method of claim 1 wherein said NO-mimetic is a member selected from the group consisting of sildenafil, cilostamide (N-cyclohexyl-N-methyl-4-(1,2-dihydro-2-oxo-6-quinolyloxy)butyramide, dipyridamole (2,6-bis (diethanol-amino)-4,8-dipipendinopyrimido-[5,4-d] pyrimidine), erythro-9-(2-hydroxy-3-nonyl)adenine (EHNA), etazolate (1-ethyl-4-[(1-methylethylidene) hydrazino]-1H-pyrazolo-[3,4-b]-pyridine-5-carboxylic acid, ethyl ester), 4-[[3,4-(methylene-dioxy)benzyl]amino]-6-chloroquinazoline (MBCQ), 8-methoxymethyl-1-methyl-3-(2-methylpropyl)xanthine (MMPX); 1-(3-chlorophenylamino)-4-phenyl-phthalazine (MY-5445); 4-(3-butoxy-4-methoxyphenyl)methyl-2-imidazolidone (Ro 20-1724), Rolipram (4-(3-(cyclopentyloxy)-4-methoxyphenyl)pyrrolidin-2-one), vinpocetine (3a, 16a)-eburnamenine-14-carboxylic acid ethyl ester), zaprinast (2-propyloxyphenyl)-8-azapurin-6-one), and zardaverine (6-[4-(difluoro-methoxy)-3-methoxyphenyl]-3(2H)-pyridazinone.

10. The method of claim 1 wherein said sleep disorder is a dyssomnia.

11. The method of claim 1 wherein said sleep disorder is a parasomnia.

12. The method of claim 1 wherein said sleep disorder is restless leg syndrome.

13. The method of claim 4 wherein said established drug for sleep disorders is a member selected from the group consisting of hypnotics, sedatives, anxiolytics, antihistamines, sedative antidepressants and dopaminergic agents.

14. The method of claim 13 wherein said established drug for sleep disorders is a member selected from the group consisting of benzodiazepine, diazepam temazepam, zoldipem, amitriptyline, trazodone, levodopa, carbidopa, bromocriptine mesylate, pergolide, codeine, propoxyphene, oxycodone, pentazocrine, hydrocodone, and methadone.

15. The method of claim 1 wherein said NO-mimetic is a compound which generates or releases NO under physiologic conditions.

* * * * *